United States Patent
Latterell et al.

(10) Patent No.: US 7,033,356 B2
(45) Date of Patent: Apr. 25, 2006

(54) BIPOLAR ELECTROSURGICAL INSTRUMENT FOR CUTTING DESICCATING AND SEALING TISSUE

(75) Inventors: Scott T. Latterell, Minneapolis, MN (US); Douglas S. Wahnschaffe, Otsego, MN (US)

(73) Assignee: Gyrus Medical, Inc., Maple Grove, MN (US)

( * ) Notice: Subject to any disclaimer, the term of this patent is extended or adjusted under 35 U.S.C. 154(b) by 0 days.

(21) Appl. No.: 10/657,378

(22) Filed: Sep. 8, 2003

(65) Prior Publication Data

US 2004/0049185 A1    Mar. 11, 2004

Related U.S. Application Data

(63) Continuation-in-part of application No. 10/188,207, filed on Jul. 2, 2002, now abandoned.

(51) Int. Cl.
*A61B 18/14* (2006.01)

(52) U.S. Cl. .............. 606/48; 606/51; 606/52

(58) Field of Classification Search ........... 606/28–31, 606/32, 39, 41, 45, 47, 49, 50–52, 48
See application file for complete search history.

(56) References Cited

U.S. PATENT DOCUMENTS

| | | | |
|---|---|---|---|
| 4,209,017 A | 6/1980 | Shaw | |
| 4,427,006 A | 1/1984 | Nottke | |
| 4,492,231 A | 1/1985 | Auth | |
| 4,655,216 A | 4/1987 | Tischer | |
| 5,190,541 A | 3/1993 | Abele et al. | |
| 5,269,780 A | 12/1993 | Roos | |
| 5,324,289 A | 6/1994 | Eggers | |
| 5,443,463 A | 8/1995 | Stern et al. | |
| 5,445,638 A | 8/1995 | Rydell et al. | |
| 5,458,598 A | 10/1995 | Feinberg et al. | |
| 5,573,424 A | 11/1996 | Poppe | |
| 5,573,535 A | 11/1996 | Viklund | |
| 5,599,350 A | 2/1997 | Schulze et al. | |
| 5,735,849 A | 4/1998 | Baden et al. | |
| 6,174,309 B1 * | 1/2001 | Wrublewski et al. | 606/45 |
| 6,187,003 B1 | 2/2001 | Buysse et al. | |

(Continued)

FOREIGN PATENT DOCUMENTS

DE    42 42 143 A1    6/1994

(Continued)

OTHER PUBLICATIONS

US 5,961,551, 10/1999, Chasak et al. (withdrawn)

*Primary Examiner*—Rosiland Rollins
(74) *Attorney, Agent, or Firm*—Thomas J. Nikolai; Nikolai & Mersereau, P.A.

(57) ABSTRACT

Electrosurgical forceps are described that have jaws capable of being closed relative to one another, the jaws each supporting electrode structures especially shaped to enhance the ability of the instrument to desiccate/seal or cut tissue structures clamped between the opposed jaws. One of the opposed jaws has a generally arcuate cross-section with a raised central zone and the other electrode has a recess adapted to accommodate the raised central zone of the cooperating electrode. By appropriating the shaping the mating electrode surfaces, tissue structures placed between the jaws are stretched laterally as clamping occurs. The stretching action prevents bunching of the tissue and results in improved desiccation, sealing and cutting. A fine, uninsulated conductor disposed on the one jaw, but insulated from the electrode surface on that jaw, serves as a cutting electrode.

16 Claims, 9 Drawing Sheets

U.S. PATENT DOCUMENTS

| | | |
|---|---|---|
| 6,270,497 B1 | 8/2001 | Sekino et al. |
| 6,273,887 B1 | 8/2001 | Yamauchi et al. |
| 6,334,860 B1 | 1/2002 | Dorn et al. |
| 6,736,813 B1 * | 5/2004 | Yamauchi et al. ............ 606/48 |
| 6,908,463 B1 | 6/2005 | Treat et al. |
| 2002/0198525 A1 | 12/2002 | Schulze et al. |
| 2003/0139741 A1 | 7/2003 | Goble et al. |
| 2004/0006340 A1 | 1/2004 | Latterell et al. |

FOREIGN PATENT DOCUMENTS

| | | |
|---|---|---|
| EP | 0 797 959 A | 1/1997 |
| EP | 1 287 788 A | 3/2003 |
| WO | WO 97/05829 A | 2/1997 |

\* cited by examiner

BIPOLAR ELECTROSURGICAL INSTRUMENT FOR CUTTING DESICCATING AND SEALING TISSUE

CROSS-REFERENCE TO RELATED APPLICATION

This application is a continuation-in-part of complete application Ser. No. 10/188,207, filed Jul. 2, 2002 now abandoned and is incorporated herein by reference in its entirety.

BACKGROUND OF THE INVENTION

I. Field of the Invention

This invention relates generally to electrosurgical instruments, and more particularly to an improved forceps whose jaws are especially designed to facilitate selective cutting, desiccation and sealing of tissue structures without the need for an instrument exchange.

II. Discussion of the Prior Art

The prior art is replete with electrosurgical forceps for use in open and laparoscopic procedures to cut through tissue structures, desiccate the tissue and any blood vessels to stem bleeding and for creating a fluid-tight seal between tissue structures along the margins of a cut. The Stern et al. U.S. Pat. No. 5,443,463 describes a coagulating forceps for use in open procedures in which the cooperating faces of its opposed jaws are generally planar and support a plurality of electrodes on one jaw and temperature sensing elements on the opposed jaw. Cutting of tissue is by way of a sharp blade that is actuated following electrocoagulation on opposed sides of the cut line.

The Fineburg U.S. Pat. No. 5,458,598 describes an endoscopic cutting and coagulating device, which, like the Stern '463 device has opposed jaw members whose opposed jaws are generally identical, each having a U-shape defining a central slot and with generally planar, albeit serrated, mating faces. A mechanical, sharpened blade, when actuated, passes longitudinally through the central slot following coagulation on each side of the cut.

The Wrublewski et al. U.S. Pat. No. 6,174,309 describes an electrosurgical instrument designed to seal and cut tissue. Embodiments for open and endoscopic procedures are described. In each case, the mating faces of the forceps jaws are such that one has raised electrode surfaces straddling a resiliently mounted cutting blade and the other has a recess for receiving the raised electrode surface therein when the jaws are closed and an intermediate groove in which the resiliently mounted cutting blade may enter. Coagulation takes place when tissue is squeezed between the jaws and a suitable voltage is applied between the raised electrodes on one jaw and on the opposite jaw. Cutting takes place when the voltage is applied between the cutting blade and the jaw having the recesses.

The Rydell et al. U.S. Pat. No. 5,445,638 describes a device somewhat similar to the Fineburg et al. '598 patent described above. It, too, has jaws having planar mating surfaces.

In each of the above-described embodiments, tissue to be coagulated, desiccated is clamped between the jaws of the device and a voltage is applied to the jaws to cause an RF current to flow through the captured tissue to heat and vaporize the moisture in the tissue. Cutting then takes place as a separate step, either by applying a cut voltage to a movable, metal blade member relative to a cooperating jaw or by effecting movement of a sharp blade through the previously desiccated tissue.

SUMMARY OF THE INVENTION

We have found that significantly improved cutting, sealing or desiccation can be achieved, when compared to prior art devices of which we are aware, by providing a forceps with non-planar mating jaw surfaces. By providing one jaw with a first electrode surface having a raised male profile and the opposite jaw with a correspondingly shaped second electrode surface defining a female recess, as tissue is being clamped therebetween, it is placed under tension and stretched slightly, which allows it to be more readily and uniformly heated when a voltage is applied between the electrodes on the opposed jaws. The tension also aids in cutting in that the shaped electrodes improves movement of the cutting electrode through tissue. As a further feature of our invention, a cutting electrode is supported on the electrode surface on one of the jaw, but is electrically isolated from that electrode surface. Switching means are then provided for applying a desiccating or sealing voltage between the first and second electrode surfaces or a cutting voltage between the cutting electrode and the first and second electrode surfaces.

Other features and advantages of the invention will become apparent from the following detailed description of a preferred embodiment, especially when considered in conjunction with the accompanying drawings in which like numerals in the several views refer to corresponding parts.

DESCRIPTION OF THE PREFERRED EMBODIMENT

Figure 1:
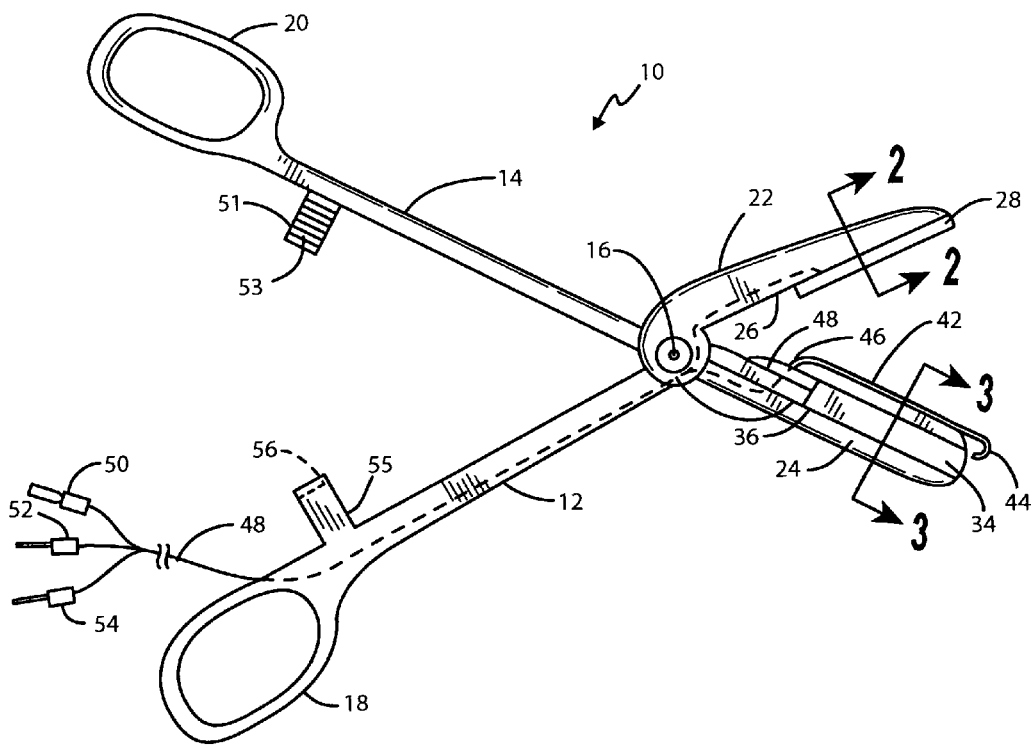
FIG. 1 is a side elevation view of an electrosurgical cutting and sealing forceps designed for use in open procedures.

Referring to FIG. 1, there is indicated generally by numeral 10 a bipolar electrosurgical forceps that is adapted to clamp, seal, desiccate and cut tissue structures in the course of an open surgical procedure, the forceps 10 includes a first forceps half 12 comprising a handle member and a second body or forceps half 14 that are electrically isolated from each other and pivotally joined by a fastener 16. The forceps halves 12 and 14 are preferably fabricated from a metal or plastic and have finger-receiving loops 18 and 20 at a proximal end thereof and jaws 22 and 24 at a distal end thereof.

Figure 2:
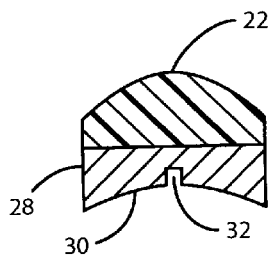
FIG. 2 is a cross-sectional view taken along the line 2—2 in FIG. 1.

Suitably fastened to a planar face 26 of the jaw 22 is a first conductive sealing electrode 28. Electrode 28 may be integral to the jaw 22. As can best be seen in the cross-sectional view of FIG. 2, the jaw/electrode 28 has obliquely extending sidewalls relative to a width axis of said jaw forming recess 30 whose arcuate sides converge to form a central, longitudinally extending notch 32 of rectangular cross-section. The exposed surfaces of the tapered arcuate recess and the notch are uninsulated.

Figure 3:
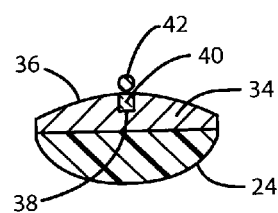
FIG. 3 is a cross-sectional view taken along the line 3—3 in FIG. 1.

The jaw 24 of the forceps half 14 has an electrode 34 either fastened to jaw surface 36 or integral with the jaw 24. As can best be seen from the cross-sectional view of FIG. 3, the electrode 34 may have a generally arcuate or beveled cross-section with obliquely extending sidewalls forming a raised dome 36 in a central zone that is adapted to fit within and conform to the recess 30 of the electrode 28. A cut electrode 42 is mounted to and extends along the length of the electrode 34, and is isolated from electrode 34 by insulating plastic or ceramic 40. As can be seen from FIG. 3, the strip 40 is generally centrally disposed at the crown of the arcuate dome 36.

Referring once more to FIG. 1, a cutting electrode 42 may comprise a thin, rigid, isolated conductor disposed on the crown of dome 36 or, alternatively, may be a fine wire that is affixed at its distal end 44 to an end surface of the insulating strip 40. The other end 46 of the wire cut electrode 42 is set in an insulating plastic 48 on the jaw 24. Thus, while the cut electrode 42 runs closely parallel to the arcuate electrode 34 (typically within about 0.025 and 0.050 inch of electrode 34), it remains electrically insulated therefrom along its entire length. While a deposited conductor or a fine wire cut electrode has been found to function well, it is to be understood that the cut electrode can be otherwise configured so as to cooperate with the jaw members in the manner described.

Routed on or through the forceps half 18 is a three conductor cord 48 having terminals 50, 52 and 54 adapted to be plugged into jacks on an electrosurgical generator or a switch box associated therewith. A first of the three wires in the cord 48 connects to the electrode 28 mounted on the jaw 22. A second conductor in the cord 48 exits the scissors half 12 proximate the pivot fastener 16 and connects to the electrode 34. The third wire in the cord 48 connects to the cut electrode 42.

In operation, tissue to be sealed and desiccated is positioned between the open jaws 24 and 26 of the forceps instrument 10 and when the forceps halves 12 and 14 are brought together, the tissue becomes squeezed between the arcuate, domed, male electrode 34 affixed to the jaw 24 and the inclined walls or electrode 38 defining the recess 30. Squeezing the finger loops 18 and 20 toward one another results in the interposed tissue being squeezed and stretched by the wiping action between the mating electrode surfaces as the two are brought together.

By applying a predetermined voltage, via the cord 48, between the electrodes 28 and 34, tissue cells are desiccated and, in case the tissue structure is tubular, the walls thereof become sealed together. The notch 32 in the electrode 28 receives the cut electrode 42 therein, allowing the electrodes 28 and 34 to close tightly on the tissue structure to be electrocoagulated.

If it is desired to maintain the tissue structure clamped between the mating electrode surfaces for a time without the need for manually gripping the finger loops 18 and 20, there is provided a tab 51 on the forceps half 14 having a plurality of parallel, saw-tooth, detent grooves 53 formed therein. A cooperating tab 55 with a barb 56 on its undersurface is formed on the forceps half 12. As the forceps handles are brought together, the barb 56 can be made to fall into one of the plurality of saw-tooth notches 53 to thereby latch the forceps jaws in their closed disposition.

When it is desired to sever the tissue structure, a second predetermined voltage is applied, via the cord 48, between the cut electrode 42 and the electrodes 28 and 34. It will be recalled that the cut wire 42 and the electrode 34 are insulated from one another by virtue of the insulating strip 40 disposed in the groove 38 of the electrode 34. By placing the lower jaw 24 beneath the tissue structure to be cut, and draping it over the surface of electrode 34 so that the tissue is brought into contact with the cut electrode 42 and jaw 34 as a predetermined voltage is applied, the tissue will be severed. Again, the shape of the jaws aids transection of tissue in that the tensioning better enables tissue to glide over the jaw/electrode.

Figure 4:
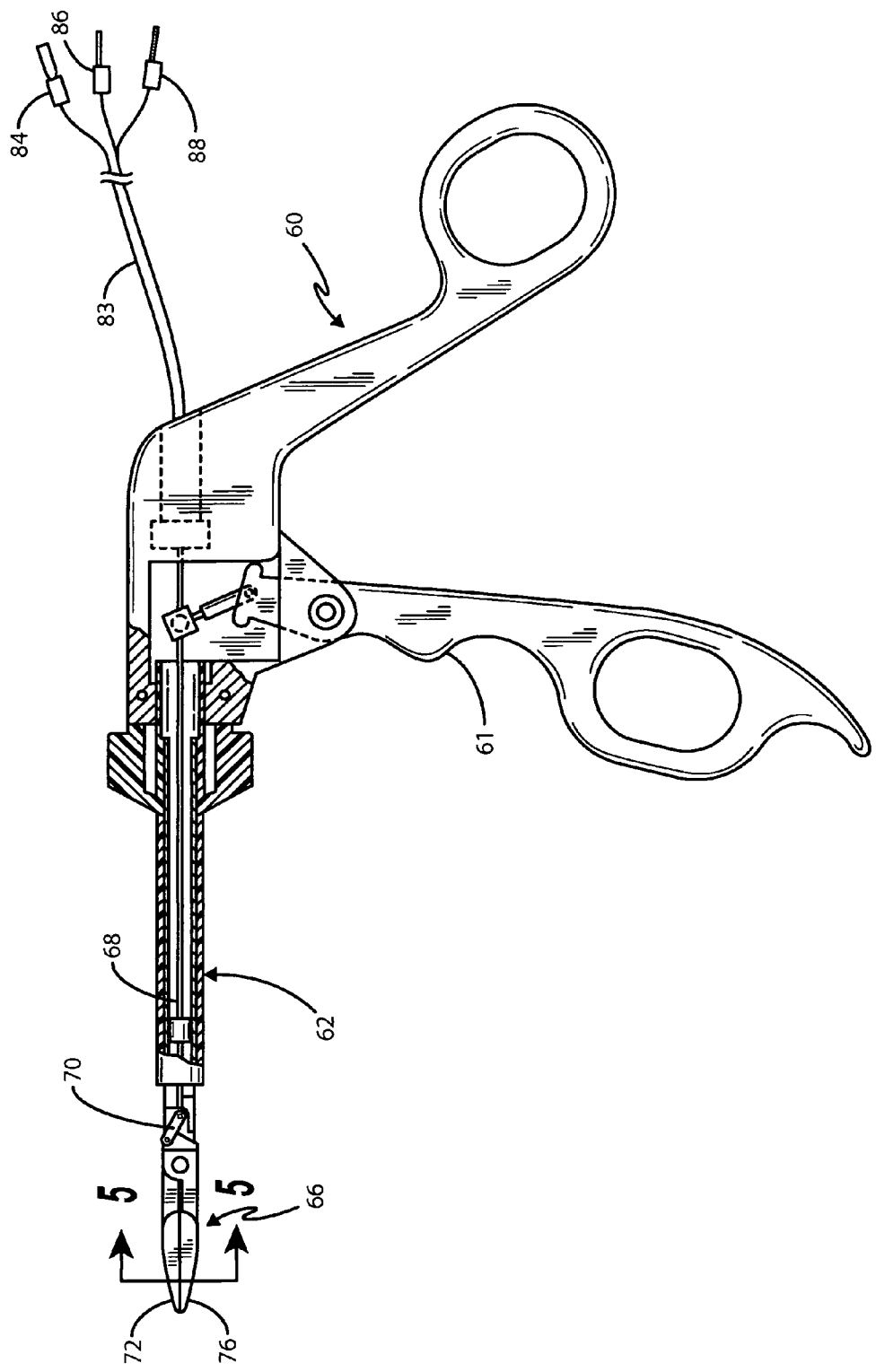
FIG. 4 is a side elevational view of an electrosurgical forceps designed for use in laparoscopic procedures and having an electrode structure in accordance with the present invention.
Figure 5:
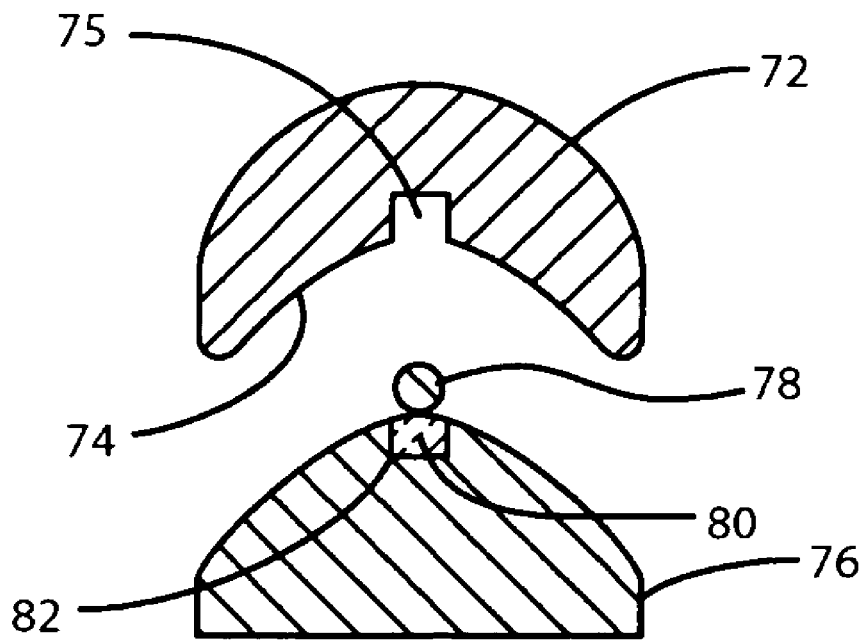
FIG. 5 is a cross-sectional view taken along the line 5—5 in FIG. 4.

A second embodiment of the invention is illustrated in FIG. 4. Here, the forceps instrument is designed for a laparoscopic procedure. The forceps of FIG. 4 includes a handle member 60 that supports an elongated barrel 62 having forceps jaws at a distal end thereof, which are indicated generally by numeral 66. The handle and mechanism for opening and closing the forceps jaws 66 relative to one another may be like that described in the Rydell U.S. Pat. No. 5,462,546, the contents of which are hereby incorporated by reference as if fully set forth herein. As is described in that patent, by manipulating the scissors-like handle 60, a push rod 68 coupled to the jaws 66 by links 70 causes the jaws to open and close relative to one another. The first jaw 72 preferably comprises a rigid metal member having a concave recess 74 and a longitudinal notch 75, as shown in the cross-sectional view of FIG. 5, which is taken along the line 5—5 in FIG. 4. The jaws may be straight and aligned with the barrel 62 or they may be curved as in the Rydell '546 patent.

The other jaw 76 of the forceps comprises a metal electrode having a generally arcuate cross-sectional shape with a raised central dome that is adapted to fit within the concave recess 74 of the jaw member 72 when the jaws 72 and 76 are made to close relative to one another. The jaw 76 also supports a fine, narrow, conductive cut electrode 78 that remains electrically insulated from a metal jaw 76 in that its proximal and distal ends are embedded in an insulating strip 80 that is fitted into a groove 82 that extends longitudinally and is formed inwardly of the crest of the arcuate surface of the jaw 76.

It can be seen that when the handle member 61 is squeezed, the jaws 66 close relative to one another while the cut electrode 78 remains electrically isolated from conductive surfaces of the jaw 76. As with the embodiment of FIG. 1, because of the shape profile of the electrode surfaces of the jaw members 72 and 76, when tissue is disposed between the jaws and the handle member 61 is squeezed, the tissue will be draped over the convex arcuate profile of the jaw electrode 76 and stretched taut by wiping action of the concave surface of jaw 72 as the two come together. Now, by applying a predetermined voltage to appropriate ones of the jacks 84, 86 or 88, a current will be made to flow between the jaws 72 and 76 through the tissue captured therebetween to effect desiccation and/or sealing of the tissue structure. When it is desired to effect cutting of the tissue, a different voltage is applied between the cut electrode 78 and the jaw electrodes 76 and 72 to effectively cut through the tissue. It is not required that the jaws 72 and 76 be closed relative to one another during a cutting operation. By placing the lower jaw 76 beneath the tissue structure to be cut and draping it over the cutting electrode 78 so that the tissue engages both the cutting electrode and the metal jaw 76, upon a slight lifting motion on the handle, application of a cutting voltage between the two will result in severing of the tissue.

Figure 6:
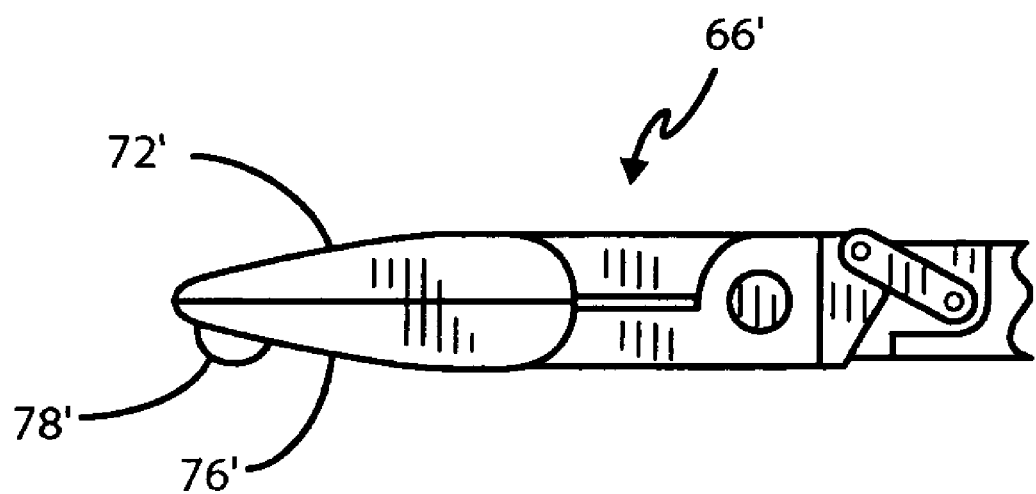
FIG. 6 is a partial view of the forceps jaws having an alternative placement for a cutting electrode.

Referring next to FIG. 6, there is shown a partial view of the forceps jaw portion of the laparoscopic instrument illustrated in FIG. 4 but with the cutting electrode disposed on an exterior surface of a jaw rather than its mating surface. In this arrangement, the jaw assembly 66' comprises a first jaw member 72' and a second jaw member 76' both being formed from a conductive material, such as stainless steel, Again, the blade assembly 66' may be rectilinear or may have a curved profile. The mating faces of the jaws are preferably contoured in the fashion indicated in FIG. 5 to provide a stretching or tensioning of tissue structures as it is being pinched between the mating jaw faces. In the embodiment of FIG. 6, however, the cutting electrode 78' is repositioned so as to be located on an outer surface of the jaw member 76' with a layer of insulating ceramic effectively electrically isolating the cut electrode 78' from the metal surface comprising the jaw member 76'. In the embodiment of FIG. 6, the cut electrode 78' is a small bump or protuberance rather than a length of wire as in the embodiment of FIG. 5.

In the arrangements of FIGS. 4 and 6, an electrical cord 83, having three insulated conductors extends through the handle 60 and into the lumen of the tubular barrel 62 so as to electrically connect, individually, to the jaws 72 and 76 and to the cut electrode 78. Connector pins 84, 86 and 88 permit the forceps instrument to be connected to a power source such as a conventional electrosurgical generator.

Figure 7:
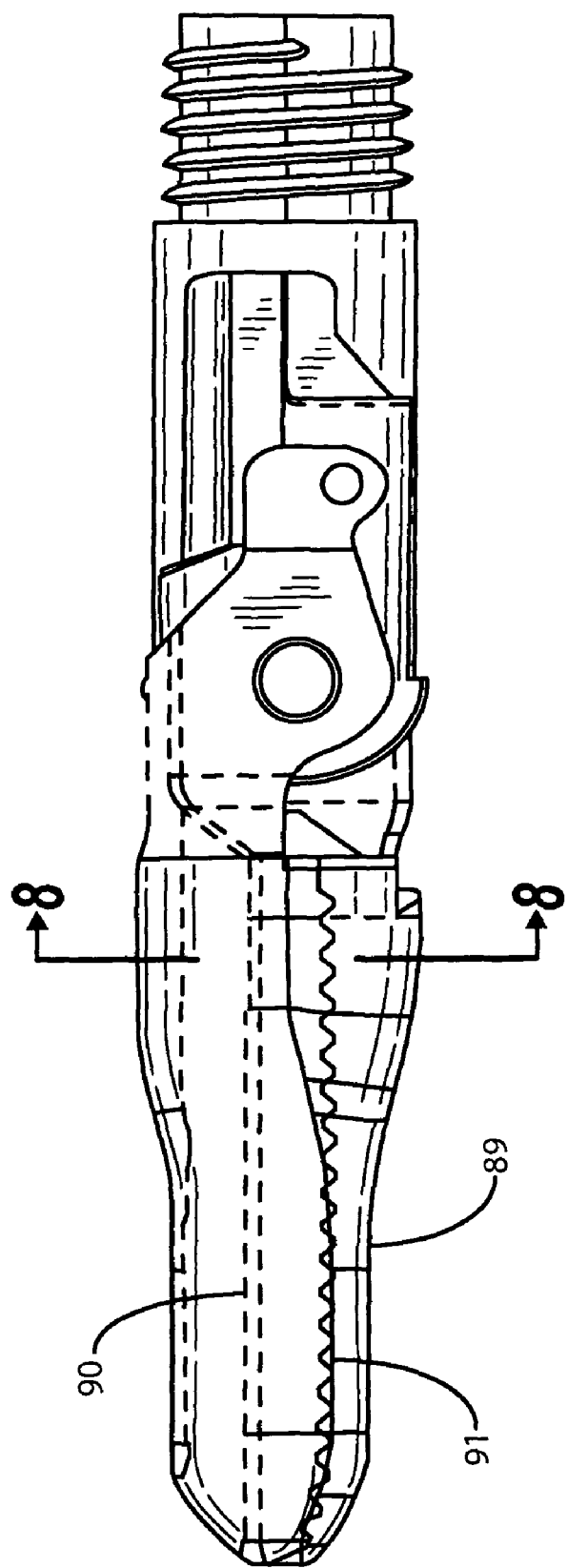
FIG. 7 is a partial side elevational view of a bipolar cutting, desiccating and sealing forceps jaw assembly fabricated in accordance with a further embodiment of the invention.

FIG. 7 shows an alternative jaw construction that is attachable to the handle mechanism of a laparoscopic forceps instrument like that of FIG. 4. Manipulation of the handle member 61 causes the jaws 89 and 90 to open and close in the manner earlier described to clamp and release tissue structures therebetween. The serrated teeth 91 on the opposed jaw surfaces allow better gripping of tissue therebetween.

Figure 8:
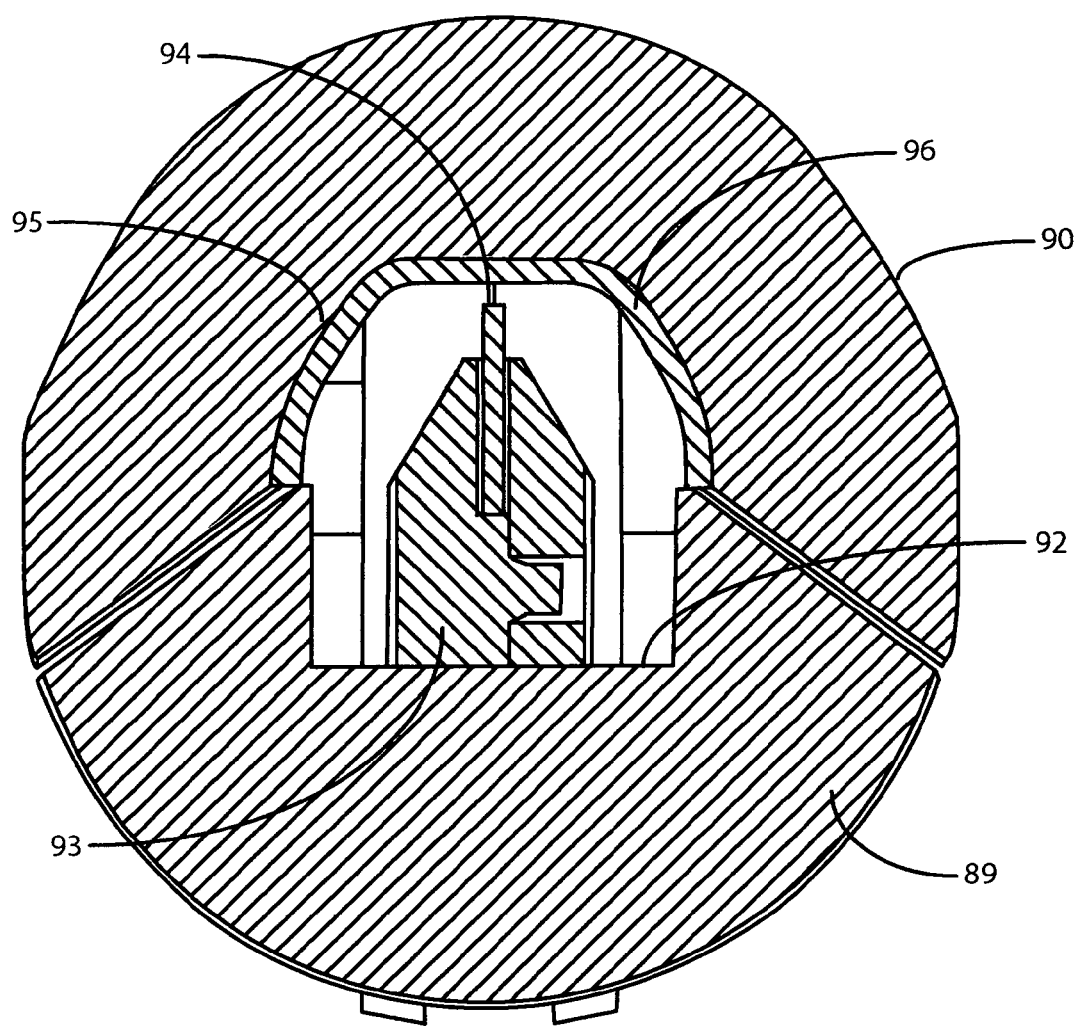
FIG. 8 is a cross-sectional view taken along the line 8—8 in FIG. 7.

Referring to the cross-sectional view of FIG. 8, the lower jaw 89 is raised and includes planar sidewalls that extend obliquely to the width axis of jaw 89 leading to a longitudinally extending slot 92. Disposed in this slot is an insulator 93, preferably of ceramic that supports a metal cutting electrode element 94. A longitudinal cavity 95 runs along the inner surface of the recessed jaw 90 and it is lined with a thin layer of insulating material 96. By providing this insulated surface, the top and bottom jaws exhibit generally equal tissue-contact areas important to providing effective tissue sealing. Planar sidewalls extend obliquely to the width axis of the jaw 90 to conform to the raised structure of jaw 89 and lead to the cavity 95.

Electrical connection to the cutting element 94 and to the jaw electrodes is provided by a cord that extends through the handle and is adapted to be connected to an electrosurgical generator in the manner previously described.

When the forceps jaws are closed about tissue to be sealed, because of the profile of the mating jaw surfaces, the tissue will be stretched slightly. When an appropriate RF voltage is applied between the closed jaws 89 and 90, an electrical current will pass through the tissue captured between the jaws to effect desiccation/sealing. If it is desired severe the tissue, a RF voltage is applied between the cutting electrode element 94 and the electrode comprising the jaw 89 and/or 90.

Figure 9:
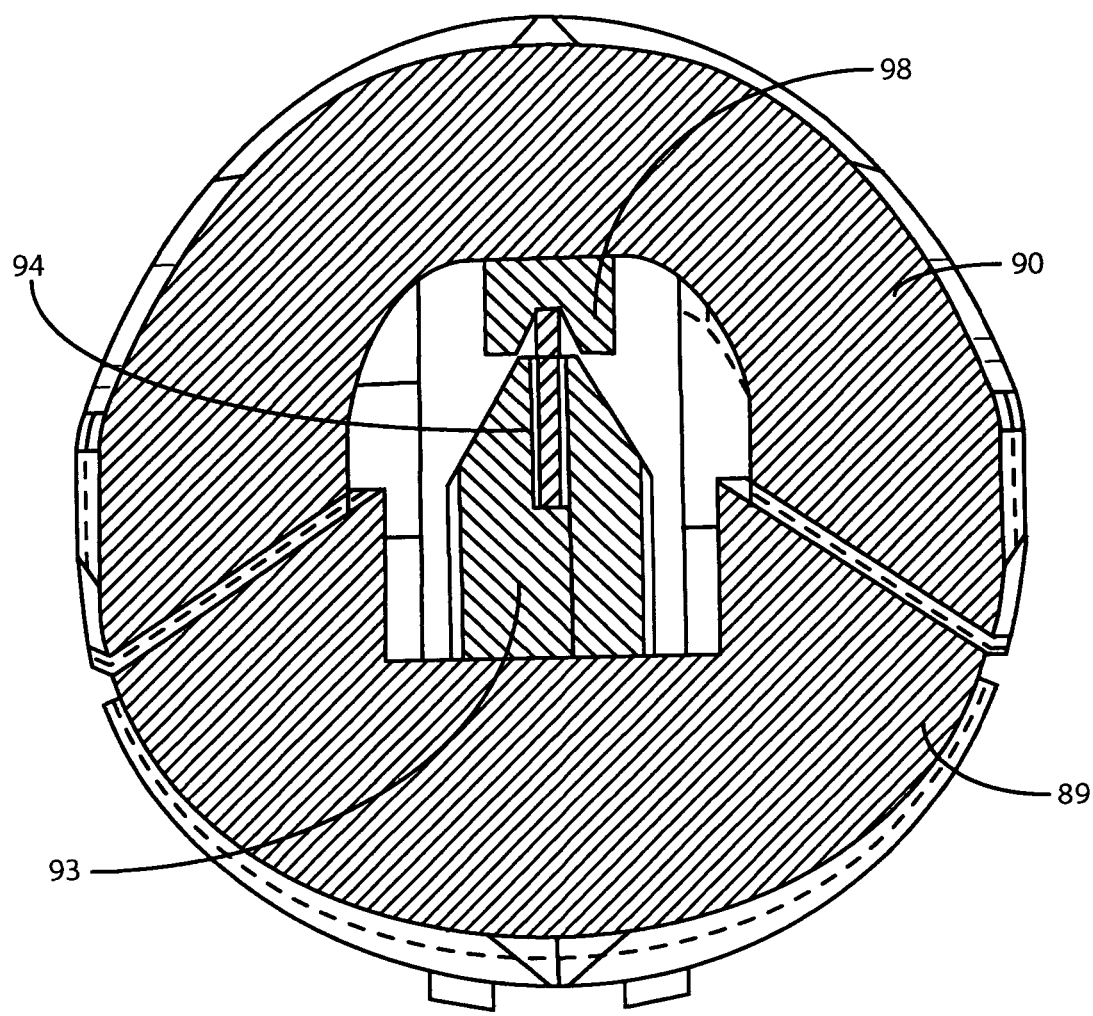
FIG. 9 is a cross-sectional view taken through the jaws of a still further embodiment in which an anvil of a compressible material is included.
Figure 10:
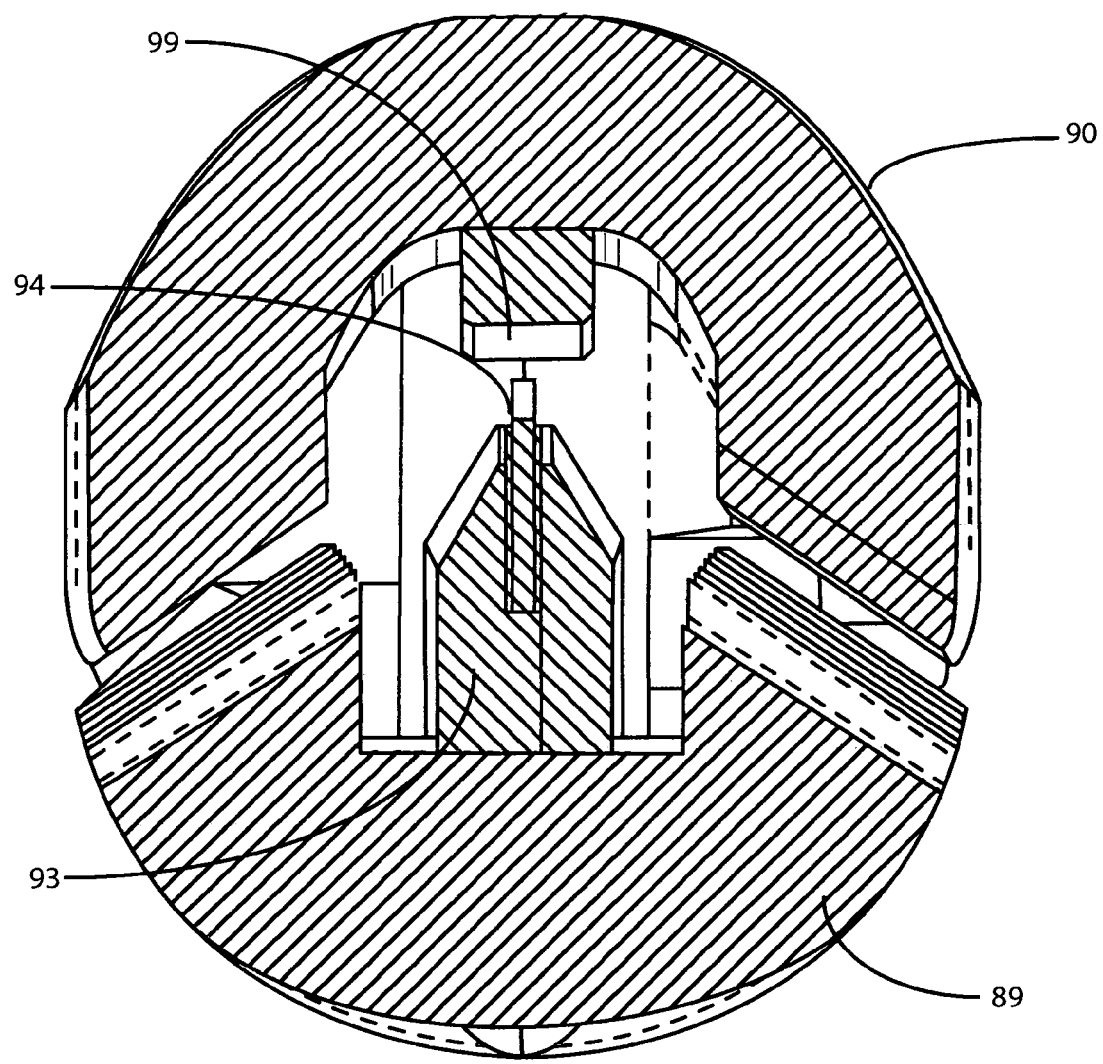
FIG. 10 is a cross-sectional view like that of FIG. 9, but with the jaws slightly parted.

Turning next to FIGS. 9 and 10, there is shown a modification that may be made to the blade structure of FIGS. 7 and 8. Here, the insulating layer 96 is replaced with a resilient strip 98 of an insulating material. A slight recess or channel 99 runs along the exposed edge of the strip. The resilient strip 98, which may be one of a number of elastomers or a spring having an insulating coating, is bonded within a hollowed-out cavity formed in the recessed jaw 90 and runs parallel to the cutting electrode 94.

FIG. 9 shows a cross-section through the jaw assembly when the jaws are squeezed together. It can be seen that the exposed cutting electrode 94 compresses the resilient insulating material 98 which, in turn, acts to push a tissue structure being severed against the cutting electrode. In the cross-section of FIG. 10, the raised jaw 89 and the recessed jaw 90 are slightly open relative to one another, showing the resilient material 98 in its undistorted condition.

In use, when the forceps jaws are clamped about a tissue structure to be cut, as the requisite voltages applied and cutting begins, the elastic properties of the resilient material supplies a force urging the tissue against the cutting electrode 94 to maintain a more uniform and consistent engagement of the tissue being severed with the cutting electrode.

Figure 11:
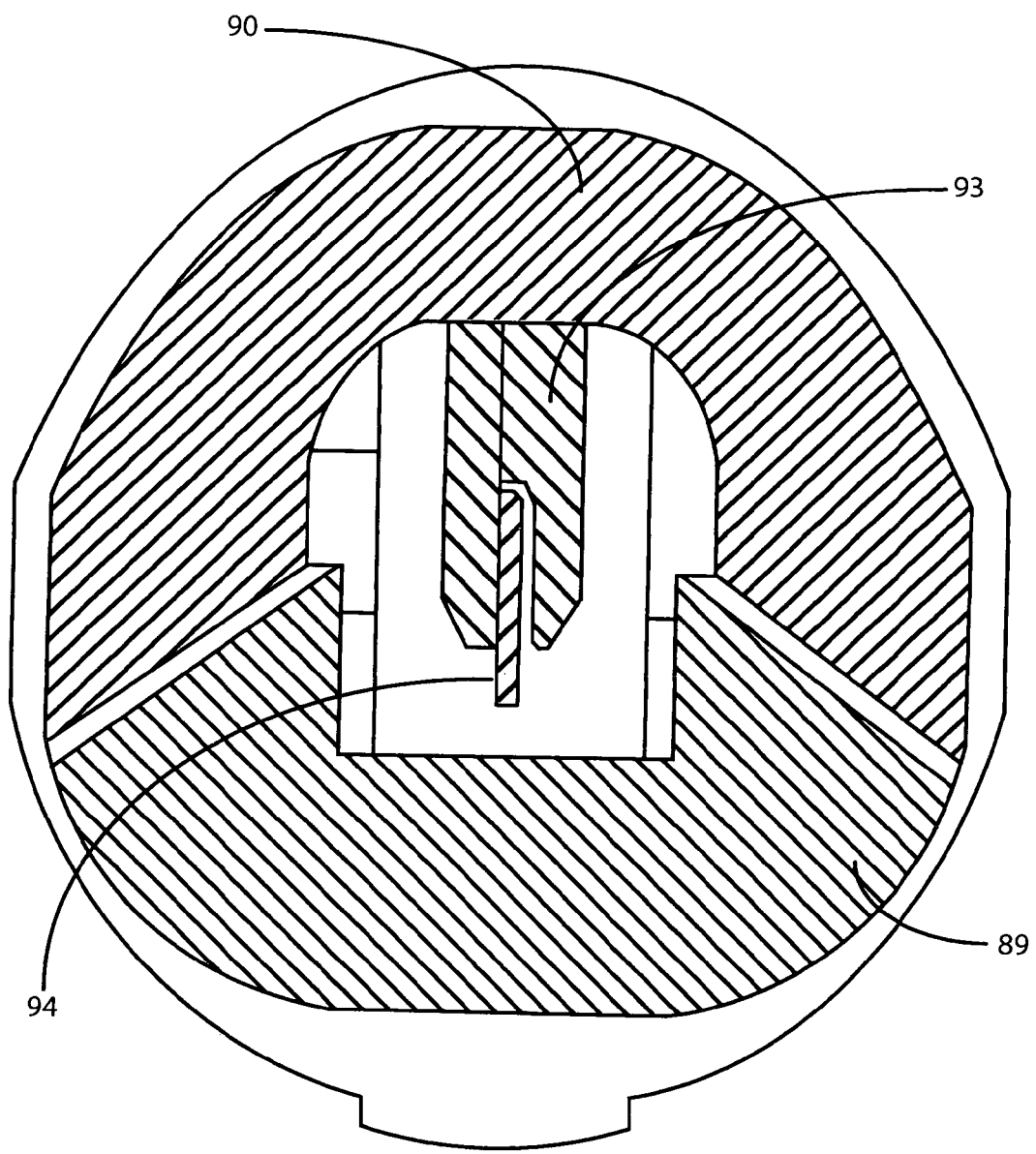
FIG. 11 is a cross-sectional view taken through the jaws of yet another embodiment of the invention.

FIG. 11 is included to illustrate that the cutting electrode element 94 and the ceramic cutting element holder 93 can be affixed to the recessed top jaw 90 instead of to the raised bottom jaw 89, as in the embodiments of FIGS. 7–10.

Figure 12:
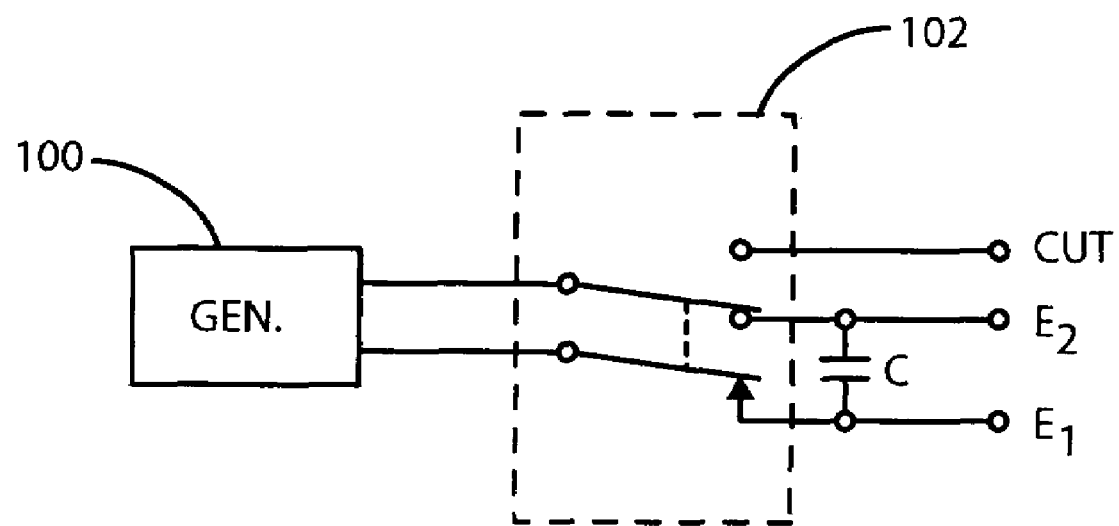
FIG. 12 is an electrical wiring diagram showing one way of switching a radio frequency electrosurgical generator to the electrodes of the forceps instruments of FIGS. 1 and 4.

FIG. 12 illustrates a switching arrangement for selectively coupling the outputs from an electrosurgical generator 100 to the three separate electrodes on the instruments of FIGS. 1, 4 and 6–11 to selectively desiccate/seal tissue structures or to sever such tissue structures. When the double pole, double throw switch 102 is in the position illustrated in FIG. 12, the RF voltage from the generator will be applied between the electrodes 28 and 34 in the embodiment of FIG. 1 or electrodes 72/72' and 76/76' in the embodiment of FIGS. 4 and 6 or electrodes 89–90 in the embodiments of FIGS. 7–11. When the switch 102 is thrown to its alternate position, a voltage for cutting tissue will be applied between the cut electrode 42 (FIG. 1) or 78 (FIG. 4) or the protuberance 78' (FIG. 6) or to the cut electrode 94 in the embodiments of FIGS. 7–11, and the electrodes 34 (FIG. 1), 76/76' (FIG. 4 or 6) or 89 (FIGS. 7–11). It may prove expedient to connect a capacitor, C, between the conductors leading to the coag electrodes 28 and 34 in the embodiment of FIG. 1 or electrodes 72 and 76 in the embodiment of FIG. 4 or 89 and 90 in the embodiments of FIGS. 7–11. The capacitor, preferably having a capacitance of about 2.2 nF, functions to create an electrical link between the coag electrodes when the cutting electrode is energized. However, when the coagulating electrodes are energized, a sufficient voltage difference is generated between the coagulating electrodes to effect sealing/coagulation. The switch may take any number of forms and it, along with capacitor, C, may be conveniently located on the instrument itself, on the electrosurgical generator or on a foot switch module often used in electrosurgical systems.

With the jaw assembly 66' on the laparoscopic instrument shown in FIG. 4 in place of the jaw assembly 66, sealing or desiccation takes place by closing the mating faces of the jaws 72' and 76' about the tissue and then applying a voltage between the two jaws causing a current flow through the captured tissue. When cutting, the voltage is preferably applied between the protuberance 78' and the jaw members 76'. When the tissue to be severed is draped over the cut electrode 78', it will also contact the jaw members 76' functioning as a return electrode. Then by gently lifting the tissue while drawing the electrode 78' thereacross, cutting occurs along a line traversed by the electrodes 78'.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself

What is claimed is:

1. A bipolar electrosurgical instrument for clamping, sealing and cutting tissue comprising:
    (a) a handle;
    (b) a body joined to the handle;
    (c) a jaw assembly joined to the body and arranged such that manipulation of the handle allows tissue at a surgical site to be clamped between opposed jaws of the jaw assembly, the jaw assembly having length, height and width axes;
    (d) a first of said opposed jaws having at least a first sealing electrode, the jaw being formed with a recess formed longitudinally along the length axis, said recess having first and second sidewalls, each side wall having at least a portion extending at an oblique angle to the width axis of the jaw assembly
    (e) the other of said opposed jaws having at least a second sealing electrode, the jaw having a cross-section exhibiting a raised central zone adapted to conform to the recess of the first jaw for pinching and tensioning the tissue when at least one of the jaws is made to close relative to the other jaw; and
    (f) a cutting electrode supported by one of said opposed jaws.

2. The bipolar electrosurgical instrument of claim 1 wherein the cutting electrode extends in spaced, centered relation along a length dimension of a sealing surface of the second sealing electrode located above and generally parallel to said central zone.

3. The bipolar electrosurgical instrument of claim 1 wherein the cutting electrode comprises a protuberance disposed on and insulated from an outer surface of the second sealing electrode.

4. The bipolar electrosurgical instrument of claim 1 wherein the body is pivotally joined to the handle.

5. The bipolar electrosurgical instrument of claim 1 wherein the body comprises an elongated tube having a lumen extending the length thereof and the handle is mechanically coupled to the first and the other of the opposed jaws through the lumen.

6. The bipolar electrosurgical instrument of claim 1 and further including switching means for selectively applying a sealing voltage between the first and second electrodes or a cutting voltage between the cutting electrode and at least one of the first and the second sealing electrodes.

7. The bipolar electrosurgical instrument of claim 6 wherein the switching means is configured to apply a cutting voltage between the cutting electrode and both said first and second sealing electrodes.

8. The bipolar electrosurgical instrument of claim 1 wherein the first of said opposed jaws includes an insulating strip that extends along a length axis of said first of said opposed jaws in alignment with said cutting electrode supported by the other of said opposed jaws.

9. The bipolar electrosurgical instrument of claim 1 wherein the cutting electrode is supported by an insulating material on one of said opposed jaws.

10. The bipolar electrosurgical instrument of claim 8 wherein the cutting electrode is supported by an insulating material on one of said opposed jaws.

11. The bipolar electrosurgical instrument of claim 8 wherein the insulating strip is a resilient structure.

12. The bipolar electrosurgical instrument of claim 11 wherein the resilient structure is compressed by the cutting electrode when at least one of the jaws is made to close relative to the other jaws to thereby apply an opposing return force to the cutting electrode.

13. The bipolar electrosurgical instrument of claim 1 wherein the cutting electrode is affixed to and electrically insulated from the first sealing member.

14. The bipolar electrosurgical instrument of claim 1 wherein the cutting electrode is affixed to and electrically insulated from the second sealing electrode.

15. The bipolar electrosurgical instrument of claim 1 wherein the sidewalls are generally planar.

16. The bipolar electrosurgical instrument of claim 1 wherein the sidewalls are arcuate.

* * * * *